(12) United States Patent
Levy (10) Patent No.: US 8,895,523 B2
(45) Date of Patent: Nov. 25, 2014

(54) USE OF ANTISENSE OLIGONUCLEOTIDES AGAINST CPLA2 IN THE TREATMENT OF CANCER

(75) Inventor: Rachel Levy, Omer (IL)

(73) Assignees: Mor Research Applications Ltd., Tel-Aviv (IL); Ben-Gurion University of the Negev Research and Development Authority, Beer-Sheva (IL)

( * ) Notice: Subject to any disclaimer, the term of this patent is extended or adjusted under 35 U.S.C. 154(b) by 0 days.

(21) Appl. No.: 12/311,419

(22) PCT Filed: Sep. 20, 2007

(86) PCT No.: PCT/IL2007/001164
§ 371 (c)(1),
(2), (4) Date: Nov. 23, 2009

(87) PCT Pub. No.: WO2008/038267
PCT Pub. Date: Apr. 3, 2008

(65) Prior Publication Data
US 2010/0204298 A1 Aug. 12, 2010

(30) Foreign Application Priority Data
Sep. 28, 2006 (IL) .......................... 178401

(51) Int. Cl.
C12N 15/11 (2006.01)
C07H 21/04 (2006.01)
C07H 21/02 (2006.01)

(52) U.S. Cl.
USPC .......................... 514/44; 536/24.5

(58) Field of Classification Search
None
See application file for complete search history.

(56) References Cited

U.S. PATENT DOCUMENTS

| | | | |
|---|---|---|---|
| 5,998,148 A | 12/1999 | Bennett | |
| 6,008,311 A | 12/1999 | Sakamoto et al. | |
| 6,008,334 A | 12/1999 | Hanna | |
| 6,008,344 A | 12/1999 | Bennett et al. | |
| 6,797,708 B2 | 9/2004 | McKew et al. | |
| 8,242,255 B2 | 8/2012 | Levy | |
| 2002/0165119 A1 | 11/2002 | Leff | |
| 2006/0014759 A1 | 1/2006 | McKew et al. | |
| 2008/0287380 A1 | 11/2008 | Levy | |
| 2012/0277292 A1 | 11/2012 | Levy | |

FOREIGN PATENT DOCUMENTS

| | | |
|---|---|---|
| EP | 0260032 | 3/1988 |
| WO | WO 00/50438 | 8/2000 |
| WO | WO 02/060535 | 8/2002 |
| WO | WO 2005/101968 | 11/2005 |
| WO | WO 2006/128142 | 11/2006 |
| WO | WO 2008/038267 | 4/2008 |

OTHER PUBLICATIONS

Dong et al (Carcinogenesis 24(2): 307-318, 2003).*
Dong et al (Clin. Cancer Res. 11: 2265-2271, 2005).*
Pirianov et al (Mol. Cell. Endocrinol. 172: 69-78, 2001).*
van Rossum et al (CMLS, Cell. Mol. Life Sci 59: 181-188, 2002).*
Dong (Cancer Letters 240: 9-16, 2006).*
Hong et al (PNAS 98(7): 3935-3939, 2001).*
Shaik et al (Int. J. Cancer, 118: 396-404, published online Jul. 28, 2005).*
Kappel et al (Curr. Opin. Biol. 3: 548-553, 1992).*
Rubenstein et al (J. Surg. Onc. 62: 194-200 (1996).*
Parhamifar et al (Carcinogenesis vol. 26 No. 11 pp. 1988-1998, 2005).*
International Search Report issued by the International Searching Authority (ISA/EP) on May 21, 2008 in connection with International Application No. PCT/IL2007/001164.
WO 2005/101968 A2 (Mor Research Applications Ltd. et al.) Nov. 3, 2005.
WO 2006/128142 A2 (Wyeth et al.) Nov. 30, 2006.
WO 00/50438 A1 (Isis Pharmaceuticals, Inc. et al.) Aug. 31, 2000.
Anderson K M, et al. "Cytosolic 85-kDa Phospholipase $A_2$-mediated Release of Arachidonic Acid Is Critical for Proliferation of Vascular Smooth Muscle Cells" The Journal of Biological Chemistry, 1997, 272(48):30504-30511.
Panel et al. "Cytoplasmic Phospholipase A2 Expression in Human Colon Adenocarcinoma Is Correlated With Cyclooxygenase-2 Expression and Contributes to Prostaglandin E2 Production", Cancer Letters, 243: 255-263, 2006.
Patel et al. "Cytosolic Phospholipase A2-α: A Potential Therapeutic Target for Prostate Cancer", Clinical Cancer Research, 14(24): 8070-8079, Dec. 15, 2008.
Weiser-Evans et al. "Depletion of Cytosolic Phospholipase A2 in Bone Marrow-Derived Macrophages Protects Against Lung Cancer Progression and Metastasis", Cnacer Research, 69(5): 1733-1738, Mar. 1, 2009.
Communication Pursuant to Article 94(3) EPC Dated Apr. 3, 2008 From the European Patent Office Re. Application No. 05731106.0.
Communication Pursuant to Article 94(3) EPC Dated Jul. 22, 2010 From the European Patent Office Re. Application No. 05731106.0.
Communication Pursuant to Rules 109 and 110 EPC Dated May 24, 2007 From the European Patent Office Re. Application No. 05731106.0.
Examiner's Report Dated Apr. 1, 2009 From the Australian Government, IP Australia Re. Application No. 2005235286.
Examiner's Report Dated Jun. 11, 2010 From the Australian Government, IP Australia Re. Application No. 2005235286.
International Preliminary Report on Patentability Dated Mar. 13, 2007 From the International Bureau of WIPO Re. Application No. PCT/IL2005/000399.
International Preliminary Report on Patentability Dated Mar. 31, 2009 From the International Bureau of WIPO Re. Application No. PCT/IL2007/001164.
International Search Report and the Written Opinion Dated May 21, 2008 From the International Searching Authority Re. Application No. PCT/IL2007/001164.
International Search Report and the Written Opinion Dated Jan. 22, 2007 From the International Searching Authority Re. Application No. PCT/IL2005/000399.
Office Action Dated Sep. 5, 2009 From the Israel Patent Office Re. Application No. 178401.

(Continued)

Primary Examiner — Richard Schnizer (57) ABSTRACT

Inhibitors of cPLA$_2$α expression are used in the preparation of pharmaceutical compositions for the inhibition of cancer cell proliferation and for the treatment of cancer; the inhibitors are selected from cPLA$_2$α-specific ribozymes, RNA sequences usable for RNA-interference of the cPLA$_2$α gene, and antisense oligonucleotides directed against cPLA$_2$α.

3 Claims, 3 Drawing Sheets

(56) References Cited

OTHER PUBLICATIONS

Office Action Dated Feb. 9, 2009 From the Israel Patent Office Re. Application No. 178764.
Office Action Dated Jul. 9, 2009 From the Israel Patent Office Re. Application No. 178401.
Office Action Dated Nov. 10, 2010 From the Israel Patent Office Re. Application No. 178764.
Official Action Dated Dec. 12, 2008 From the US Patent and Trademark Office Re. U.S. Appl. No. 11/568,169.
Official Action Dated Apr. 21, 2009 From the US Patent and Trademark Office Re. U.S. Appl. No. 11/568,169.
Official Action Dated Jul. 23, 2009 From the US Patent and Trademark Office Re. U.S. Appl. No. 11/568,169.
Official Action Dated Oct. 23, 2009 From the US Patent and Trademark Office Re. U.S. Appl. No. 11/568,169.
Official Action Dated Jul. 27, 2010 From the US Patent and Trademark Office Re. U.S. Appl. No. 11/568,169.
Official Action Dated Jan. 28, 2010 From the US Patent and Trademark Office Re. U.S. Appl. No. 11/568,169.
Response Dated Nov. 5, 2009 to Office Action of Jul. 9, 2009 From the Israel Patent Office Re. Application No. 178401.
Response Dated Jan. 6, 2011 to Communication Pursuant to Article 94(3) EPC Dated Jul. 22, 2010 From the European Patent Office Re. Application No. 05731106.0.
Response Dated May 6, 2009 to Office Action of Jan. 14, 2009 From the Israel Patent Office Re. Application No. 178401.
Response Dated Jul. 7, 2008 to Communication Pursuant to Article 94(3) EPC of Apr. 3, 2008 From the European Patent Office Re. Application No. 05731106.0.
Response Dated May 11, 2009 to Official Action of Apr. 21, 2009 From the US Patent and Trademark Office Re. U.S. Appl. No. 11/568,169.
Response Dated Mar. 16, 2009 to Official Action of Dec. 12, 2008 From the US Patent and Trademark Office Re. U.S. Appl. No. 11/568,169.
Response Dated Nov. 20, 2009 to Official Action Dated Oct. 23, 2009 From the US Patent and Trademark Office Re. U.S. Appl. No. 11/568,169.
Response Dated Aug. 24, 2009 to Official Action of Jul. 23, 2009 From the US Patent and Trademark Office Re. U.S. Appl. No. 11/568,169.
Response Dated May 27, 2010 to Examiner's Report of Apr. 1, 2009 From the Australian Government, IP Australia Re. Application No. 2005235286.
Response Dated May 28, 2010 to Official Action of Jan. 28, 2010 From the US Patent and Trademark Office Re. U.S. Appl. No. 11/568,169.
Response Dated Jun. 29, 2010 to Examiner's Report of Jun. 11, 2010 From the Australian Government, IP Australia Re. Application No. 2005235286.
Response Dated May 31, 2009 to Office Action of Feb. 9, 2009 From the Israel Patent Office Re. Application No. 178764.
Supplementary European Search Report Dated Nov. 27, 2007 From the European Patent Office Re. Application No. 05731106.0.
Supplementary Partial European Search Report Dated Oct. 9, 2007 From the European Patent Office Re. Application No. 05731106.0.
Translation of Notification of the First Office Action Dated Oct. 9, 2010 From the State Intellectual Property Office of the People's Republic of China Re. Application No. 200580012674.2.
Allawi et al. "Mapping of RNA Accessible Sites by Extension of Random Oligonucleotide Libraries With Reverse Transcriptase", RNA, 7: 314-327, 2001.
Anderson et al. "Cytosolic 85-kDa Phospholipase A2-Mediated Release of Arachidonic Acid Is Critical for Proliferation of Vascular Smooth Muscle Cells", The Journal of Biological Chemistry, XP002478503, 272(48): 30504-30511, Nov. 28, 1997.
Bendele et al. "Combination Benefit of Treatment With the Cytokine Inhibitors Interleukin-1 Receptor Antagonist and PEGylated Soluble Tumor Necrosis Factor Receptor Type I in Animal Models of Rheumatoid Arthritis", Arthritis & Rheumatism, 43(12): 2648-2659, Dec. 2000.
Chalk et al. "Computational Antisense Oligo Prediction With a Neural Network Model", Bioinforamtics, 18(12): 1567-1575, 2002.
Dana et al. "Essential Requirement of Cytosolic Phospholipase A2 for Activation of the Phagocyte NADPH Oxidase", The Journal of Biological Chemistry, 273(1): 441-445, Jan. 2, 1998.
Dana et al. "The Requirement for Phospholipase A2 for Activation of the Assembled NADPH Oxidase in Human Neutrophils", Biochemistry Journal, 297: 217-223, 1994.
Gij ?n et al. "Cytosolic Phospholipase A2 Is Required for Macrophage Arachidonic Acid Release by Antagonists That Do and Do Not Mobilize Calcium", The Journal of Biological Chemistry, 275(26): 20146-20156, Jun. 30, 2000.
Greenbaum et al. "Comparing Protein Abundance and mRNA Expression Levels on a Genomic Scale", Genome Biology, 4(9/Art. 117): 117.1-117.8, 2003.
Griffoni et al. "The Rossmann Fold of Glyceraldehyde-3-Phosphate Dehydrogenase (GAPDH) Is a Nuclear Docking Site for Antisense Oligonucleotides Containing a Taaat Motif", Biochimica et Biophysica Acta, XP002452585, 1530(1): 32-46, Jan. 15, 2001. Relevant to Inventions 1, 2, 5.
Hazan et al. "Cytosolic Phospholipase A2 and its Mode of Activation in Human Nutrophils by Opsonized Zymosan. Correlation Between 42/44 kDa Mitogen-Activated Protein Kinase, Cytosolic Phospholipase A2 and NADPH Oxidase", Biochemistry Journal, 326: 867-876, 1997.
Hazan-Halevy et al. "The Requirement of Both Extracellular Regulated Kinase and P38 Mitogen-Activated Protein Kinase for Stimulation of Cytosolic Phospholipase A2 Activity by Either Fc?RIIA or Fc?RIIIB in Human Neutrophils. A Possible Role for Pyk2 But Not for the Grb2-Sos-Shc Complex", The Journal of Biological Chemistry, 275(17): 12416-12423, Apr. 28, 2000.
Jaeger et al. "Predicting Optimal and Suboptimal Secondary Structure for RNA", Methods in Enzymology, 183: 281-306, 1990.
Jansen et al. "Chemosensitisation of Malignant Melanoma by BCL2 Antisense Therapy", The Lancet, 356: 1728-1733, Nov. 18, 2000.
Kalyvas et al. "Cytosolic Phospholipase A2 Plays a Key Role in the Pathogenesis of Multiple Sclerosis-Like Disease", Neuron, XP002414424, 41: 323-335, Feb. 5, 2004. p. 323.
Kiaei et al. Integrative Role of cPLA2 With COX-2 and the Effect of Non-Steriodal Anti-Inflammatory Drugs in a Transgenic Mouse Model of Amyotrophic Lateral Sclerosis, Journal of Neurochemistry, 93: 403-411, 2005. p. 403-404.
Laktionov et al. "Knock Down of Cytosolic Phospholipase A2: An Antisense Oligonucleotide Having a Nuclear Localization Binds a C-Terminal Motif of Glyceraldehyde-3-Phosphate Dehydrogenase", Biochimca et Biophysica Acta, 1636: 129-135, 2004.
Levy et al. "Effect of 1,25-Dihydroxyvitamin D3, Lipopolysaccharide, or Lipoteichoic Acid on the Expression of NADPH Oxidase Components in Cultured Human Monocytes", The Journal of Immunology, 147(9): 3066-3071, Nov. 1, 1991.
Levy et al. "Elevated Cytosolic Phospholipase A2 Expression and Activity in Human Neutrophils During Sepsis", Blood, 95: 660-665, 2000.
Levy et al. "Elevated NADPH-Oxidase Activity in Neutrophils From Bile-Duct-Ligated Rats: Changes in the Kinetic Parameters and in the Oxidase Cytosolic Factor P47", Biochimica et Biophysica Acta, 1220: 261-265, 1994.
Levy et al. "Potential Use of Tuftsin in Treatment of Candida Peritonitis in a Murine Model", Journal of Biological Regulators and Homeostatic Agents, 3(2): 71-78, 1989.
Levy et al. "The Requirementof P47 Phosphorylation for Activation of NADPH Oxidase by Opsonized Zymosan in Human Neutrophils", Biochimica et Biophysica Act, 1220: 253-260, 1994.
Li et al. "Selective Inhibition of Cytosolic Phospholipase A2 in Activated Human Monocytes", The Journal of Biological Chemistry, 002924797, 272(4): 2404-2411, Jan. 24, 1997. p. 2406, col. 1, § 3-4, Relevant to Inventions 1, 2, 5.

(56) References Cited

OTHER PUBLICATIONS

Locati et al. "Inhibition of Monocyte Chemotaxis to C-C Chemokines by Antisense Oligonucleotide for Cytosolic Phospholipase A2", The Journal of Biological Chemistry, 271(11): 6010-6016, Mar. 15, 1996.
Lowenthal et al. "Essential Requirement of Cytosolic Phospholipase A2 for Activation of the H+ Channel in Phagocyte-Like Cells", The Journal of Biological Chemistry, 274(31): 21603-21608, Jul. 30, 1999.
Marshall et al. "Depletion of Human Monocyte 85-kDa Phospholipase A2 Does Not Alter Leukotriene Formation", The Journal of Biological Chemistry, 272(2): 759-765, Jan. 10, 1997.
Muthalif et al. "Calcium/Calmodulin-Dependent Protein Kinase II? Mediates Activation of Mitogen-Activated Protein Kinase and Cytosolic Phospholipase A2 in Norepinephrine-Induced Arachidonic Acid Release in Rabbit Aortic Smooth Muscle Cells", The Journal of Biological Chemistry, 271(47): 30149-30157, Nov. 22, 1996.
Persaud et al. "A Key Role for β-Cell Cytosolic Phospholipase A2 in the Maintenance of Insulin Stores But Not in the Initiation of Insulin Secretion", Diabetes, XP002452586, 51(1): 98-104, Jan. 2002. Relevant to Inventions 1, 2, 5.
Pessach et al. "Essential Requirement of Cytosolic Phospholipase A2 for Stimulation of NADPH Oxidase-Associated Diaphorase Activity in Granulocyte-Like Cells", The Journal of Biological Chemistry, 276(36): 33495-33503, Sep. 7, 2001.
Pirollo et al. "Antisense Therapeutics: From Theory to Clinical Practice", Pharmacology & Therapeutics, 99: 55-77, 2003.
Riesenberg et al. "Neutrophil Superoxide Release and Interleukin 8 in Acute Myocardial Infarction: Distinction Between Complicated and Uncomplicated States", European Journal of Clinical Investigation, 27: 398-404, 1997.
Roshak et al. "Suppression of Monocyte 85-kDa Phospholipase A2 by Antisense and Effects on Endotoxin-Induced Prostaglandin Biosynthesis", The Journal of Biological Chemistry, 269(42): 25999-26005, Oct. 21, 1994.
Rubin et al. "Cytosolic Phospholipase A2-? Is Necessary for Platelet-Activating Factor Biosynthesis, Efficient Neutrophil-Mediated Bacterial Killing, and the Innate Immune Response to Pulmonary Infection", The Journal of Biological Chemistry, 280(9): 7519-7529, Mar. 4, 2005.
Scherr et al. "RNA Accessibility Prediction: A Theoretical Approach Is Consistent With Experimental Studies in Cell Extracts", Nucleic Acids Research, 28(13): 2455-2461, 2000.
Segal et al. "Thioglycollate Peritonitis in Mice Lacking C5, 5-Lipoxygenase, or P47phox: Complement, Leukotrienes, and Reactive Oxidants in Acute Inflammation", Journal of Leukocyte Biology, 71: 410-416, Mar. 2002.
Shaked et al. "Superoxide Production by Neutrophils From Trauma Patients: Regulation of NADPH Oxidase Activity", The Journal of Trauma, 37(1): 22-29, 1994.
Shmelzer et al. "Cytosolic Phospholipase A2? Is Targeted to the P47phox-PX Domain of the Assembled Nadph Oxidase Via a Novel Binding Site in Is C2 Domain", The Journal of Biological Chemistry, 283(46): 31898-31908, Nov. 14, 2008.
Shmelzer et al. "Unique Targeting of Cytosolic Phosphpolipase A2 to Plasma Membranes Mediated by the NADPH Oxidase in Phagocytes", The Journal of Cell Biology, 162(4): 683-692, Aug. 18, 2003.
Sohail et al. "Selecting Optimal Antisense Reagents", Advanced Drug Delivery Reviews, 44: 23-34, 2000.
Stein et al. "Physicochemical Properties of Phosphorothioate Oligodeoxynucleotides", Nucleic Acids Research, 16(8): 3209-3221, 1988.
Tarsi-Tsuk et al. "Stimulation of the Respiratory Burst in Peripheral Blood Monocytes by Lipoteichoic Acid", The Journal of Immunology, 144(7): 2665-2670, Apr. 1, 1990.
Tommasini et al. "Hydrogen Peroxide Generated at the Level of Mitochondria in Response to Peroxynitrite Promotes U937 Cell Death Via Inhibition of the Cytoprotective Signalling Mediated by Cytosolic Phospholipase A2", Cell Death and Differentiation, 11: 974-984, 2004. p. 974.
Zhang et al. "Antisense Inhibition of the Photosystem I Antenna Protein Lhca4 in *Arabidopsis thaliana*", Plant Physiology, 115: 1525-1531, 1997.
Zhao et al. "Cytosolic Phospholipase A2 (cPLA2) Regulation of Human Monocyte Nadph Oxidase Activity", The Journal of Biological Chemistry, 277(28): 25385-25392, Jul. 12, 2002.
Examination Report Dated Feb. 21, 2012 From the Government of India, Patent Office, Intellectual Property Building Re. Application No. 6394/DELNP/2006.
Official Action Dated Feb. 20, 2013 From the US Patent and Trademark Office Re. U.S. Appl. No. 13/547,113.
Patil et al. "DNA-Based Therapeutics and DNA Delivery Systems: A Comprehensive Review", The AAPS Journal, 7(1): E61-E77, 2005.
Office Action Dated Feb. 15, 2012 From the Israel Patent Office Re. Application No. 178764 and Its Translation Into English.
Response Dated Jan. 12, 2011 to Office Action Dated Sep. 5, 2009 From the Israel Patent Office Re. Application No. 178401.
Response Dated Jan. 27, 2011 to Official Action of Jul. 27, 2010 From the US Patent and Trademark Office Re. U.S. Appl. No. 11/568,169.
Official Action Dated Jun. 11, 2013 From the US Patent and Trademark Office Re. U.S. Appl. No. 13/547,113.
Office Action Dated Jun. 28, 2011 From the Israel Patent Office Re. Application No. 178764 and Its Translation Into English.
Official Action Dated Jul. 27, 2011 From the US Patent and Trademark Office Re. U.S. Appl. No. 11/568,169.
Dias et al. "Potential Roles of Antisense Oligonucleotides in Cancer Therapy. The Example of Bcl-2 Antisense Oligonucleotides", European Journal of Pharmaceutics and Biopharmaceutics, 54: 263-269, 2002.
Patel et al. "Cytosolic Phospholipase A2-?: A Potential Therapeutic Target for Prostate Cancer", Clinical Cancer Research, 14(24): 8070-8079, Dec. 15, 2008.
Persaud et al. "A Key Role for ?-Cell Cytosolic Phospholipase A2 in the Maintenance of Insulin Stores But Not in the Initiation of Insulin Secretion", Diabetes, XP002452586, 51(1): 98-104, Jan. 2002. Relevant to Inventions 1, 2, 5.
Neufert et al. "An Inducible Mouse Model of Colon Carcinogenesis for the Analysis of Sporadic and Inflammation-Driven Tumor Progression", Nature Protocols, 2(8): 1998-2004, 2007.
Official Action Dated Nov. 29, 2011 From the US Patent and Trademark Office Re. U.S. Appl. No. 11/568,169.
Clark et al. "Potential Therapeutic Uses of Phospholipase A2 Inhibitors", Expert Opinion on Therapeutic Patents, XP002405708, 14(7): 937-950, 2004.
Response Dated Mar. 10, 2011 to Office Action of Nov. 10, 2010 From the Israel Patent Office Re. Application No. 178764.
Advisory Action Before the Filing of an Appeal Brief Dated Sep. 16, 2013 From the US Patent and Trademark Office Re. U.S. Appl. No. 13/547,113.
Response Dated Oct. 30, 2011 to Office Action of Jun. 28, 2011 From the Israel Patent Office Re. Application No. 178764.
Official Action Dated Jul. 11, 2011 From the US Patent and Trademark Office Re. U.S. Appl. No. 11/568,169.
Response Dated Oct. 11, 2011 to Official Action of Jul. 11, 2011 From the US Patent and Trademark Office Re. U.S. Appl. No. 11/568,169.
Interview Summary Dated Jan. 24, 2011 From the US Patent and Trademark Office Re. U.S. Appl. No. 11/568,169.
Restriction Official Action Dated Dec. 7, 2012 From the US Patent and Trademark Office Re. U.S. Appl. No. 13/547,113.
Notice of Omitted Item(s) in a Nonprovisional Application Dated Mar. 24, 2014 From the US Patent and Trademark Office Re. U.S. Appl. No. 14/201,970.
Advisory Action Before the Filing of an Appeal Brief Dated Dec. 5, 2013 From the US Patent and Trademark Office Re. U.S. Appl. No. 13/547,113.
Hearing Notice Dated Jan. 13, 2014 From the Government of India, Patent Office, intellectual Property Building Re. Application No. 6394/DELNP/2006.

(56) References Cited

OTHER PUBLICATIONS

Summons to Attend Oral Proceedings Pursuant to Rule 115(1) EPC Dated Feb. 26, 2014 From the European Patent Office Re. Application No. 05731106.0.

Official Action Dated Sep. 9, 2014 From the US Patent and Trademark Office Re. U.S. Appl. No. 14/201,970.

Farooqui et al. "Inhibitors of Brain Phospholipase A2 Activity: Their Neuropharmacological Effects and Therapeutic Importance for the Treatment of Neurologic Disorders", Pharmacological Reviews, 58(3): 591-620, 2006.

Lee et al. "Brain Arachidonic Acid Cascade Enzymes Are Upregulated in a Rat Model of Unilateral Parkinson Disease", Neurochemical Research, 35: 613-619, 2010.

Smesny et al. "Decreased Phospholipase A2 Activity in Cerebrospinal Fluid of Patients With Dementia", Journal of Neural Transmission, 115: 1173-1179, 2008.

* cited by examiner

TIME (hours)

Fig. 3d

```
SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
ttcaaaggtc tcattccaca                                                 20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
cactataatg tgctggtaag                                                 20

<210> SEQ ID NO 3
<211> LENGTH: 21
<212> TYPE: DNA
<213> ORGANISM: Artificial Sequence
<220> FEATURE:
```

```
<223> OTHER INFORMATION: Chemically Synthesized

<400> SEQUENCE: 3
caaaacattt tcctgattag g                                              21

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
cacagggttt atgtcattat                                                20

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
ccgtaaactt gtgggaatac                                                20

<210> SEQ ID NO 6
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 6
gctgtcaggg gttgtag                                                   17

<210> SEQ ID NO 7
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 7
caccaaagtg acaaaggg                                                  18

<210> SEQ ID NO 8
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 8
gctttaacat tttattttat ttg                                            23

<210> SEQ ID NO 9
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 9
acagttcttg gcatttgttc tc                                             22
```

```
<210> SEQ ID NO 10
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 10
gtagaagagg tactttaagy ttg                                              23

<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 11
agtcaatggc atcgcgggc tgg                                               23
```

USE OF ANTISENSE OLIGONUCLEOTIDES AGAINST CPLA2 IN THE TREATMENT OF CANCER

RELATED APPLICATIONS

This application is a §371 national stage of PCT International Application No. PCT/IL2007/001164, filed Sep. 20, 2007, and claims priority of Israeli Patent Application No. 178401, filed Sep. 28, 2006, the contents of all of which are hereby incorporated by reference into this application.

FIELD OF THE INVENTION

The present invention relates to the field of anti-cancer agents. More specifically, the present invention relates to the inhibition of cytosolic phospholipase $A_2$ ($cPLA_2$) and its resulting anti-neoplastic effect. Particularly, the present invention relates to anti-$cPLA_2$ antisense oligonucleotides and their anti-proliferative properties in cancer cells.

BACKGROUND OF THE INVENTION

Cytosolic phospholipase $A_2$ ($cPLA_2$) has been suggested to be the major isozyme responsible for production of arachidonic acid (AA), the precursor of eicosanoids and to regulate the DNA-binding ability of NFkB. Four different human $cPLA_2$s have been isolated and classified into groups IVA, IVB, IVC, IVD, respectively. Of these isoforms, $cPLA_2\alpha$ has been studied most extensively. $cPLA_2\alpha$ is an 85 kDa serine esterase, which is found in a wide range of tissues except lymphocytes. By contrast, $cPLA_2\beta$ is a 114 kDa enzyme expressed predominantly in the cerebellum and pancreas, and $cPLA_{2\gamma}$ is a 61 kDa enzyme expressed predominantly in skeletal muscle. In its inactive state, $cPLA_2\alpha$ is located within the cytosol of the cell. $cPLA_2\delta$ was identified in association with psoriasis. Activation of $cPLA_2\alpha$ is regulated by cytoplasmic $Ca^{2+}$ levels and by phosphorylation, which, in turn, causes its translocation from the cytosol to perinuclear membranes, such as the Golgi, the endoplasmic reticulum and the nuclear envelope. $cPLA_2\alpha$ has been shown to be highly selective towards phospholipids that have AA at the sn-2 position. The translocation of $cPLA_2\alpha$ is important for at least two reasons: firstly, it enables interaction between the enzyme and its substrate membrane phospholipids, and secondly, it brings the enzyme into close proximity to other downstream enzymes involved in eicosanoid synthesis, specifically COX and LOX.

Although $cPLA_2\alpha$ is expressed in several tissue types, its elevated expression has been demonstrated in a range of human tumor types, such as colorectal cancer, small bowel adenocarcinoma, pancreatic adenocarcinoma, esophageal squamous cell carcinoma and lung cancer. Thus, $cPLA_2\alpha$ has been postulated to be involved in the pathogenesis of cancer [Laye, J. P. et al. (2003) *Drug Discovery Today*, 8: 710-6]. Within these tumors, high levels of AA and eicosanoids are observed as a consequence of increased activity of $cPLA_2\alpha$ and the COX and LOX enzymes. Like $cPLA_2\alpha$, elevated levels of COX-2 have been associated with human tumourigenesis. Accordingly, selective inhibition of COX-2 activity has attracted considerable interest as an anti-cancer therapeutic strategy. Acetylsalicylic acid (ASA), the most commonly COX-2 inhibitor used, has been shown to reduce the risk for colorectal cancer by as much as approximately 40% In addition, ASA was reported to reduce the risk of colorectal adenoma and carcinoma, as well as experimental colon cancer.

Recently, in human non-small-cell lung cancers, expression of oncogenic forms of Ras were associated with increased expression and activity of $cPLA_2\alpha$—a relationship that was strengthened by the observation that Ras inhibition led to decreased $cPLA_2\alpha$ phosphorylation as well as expression, and to prostaglandin synthesis.

Homozygous deletion of the $cPLA_2\alpha$ gene in mice resulted in an 83% decrease in small intestinal polyp number and an accompanying decrease in polyp size. The intestinal epithelium in $cPLA_2\alpha$ null mice contained numerous small ulcerative lesions, indicating that $cPLA_2\alpha$ has a role in tumor promotion, rather than tumor initiation. When compared to wild type, $cPLA_2\alpha$ null mice developed 43% fewer urethane induced tumors, indicating a role for $cPLA_2\alpha$ in mouse lung tumorigenesis. $cPLA_2$, COX-1, COX-2 and microsomal $PGE_2$ synthase, examined by immunohistochemistry, are present in alveolar and bronchiolar epithelia and in alveolar macrophages in lungs from naïve mice and tumor-bearing mice. Tumors express higher levels of $cPLA_2$, COX-1, COX-2 and microsomal $PGE_2$ synthase when compared to control lungs. Recently, studies have suggested that the effects of $cPLA_2\alpha$ on tumor formation might be tissue-specific. Whereas homozygous deletion of $cPLA_2\alpha$ produced a significant reduction in tumor number in the murine small intestine, no significant effect was observed in the large intestine [Hong, K. H. et al. (2001). *Proc. Natl. Acad. Sci. USA*. 98, 3935-3939; Takaku, K. et al. (2000) *J. Biol. Chem.* 275, 34013-6].

Although the use of COX-2-specific inhibitors, such as ASA, avoids the deleterious side effect of COX-1 inactivation, many of these selective drugs have complications, as a consequence of shifting AA metabolism from the inhibited COX-2 enzyme to alternative pathways, such as COX-1 and LOX and accelerate their activity. Hence, there is a need for alternative therapeutic approaches which would avoid the complications of COX-2 inhibition by limiting AA availability and subsequent eicosanoid production.

Antisense oligonucleotides targeted against the $cPLA_2$ mRNA sequence have been reported in the past as capable of inhibiting $cPLA_2$ transcript expression [U.S. Pat. No. 6,008, 344]. However, these oligonucleotides did not demonstrate inhibition of $cPLA_2$ protein expression, and were introduced into cells in the presence of lipofectin.

In addition, three other antisense oligonucleotides targeted to $cPLA_2$ have been described [Roshak, A. (1994) *J. Biol. Chern.* 269(42): 25999-26005; Muthalif, M. M. et al. (1996) *J. Biol. Chem.* 271(47): 30149-30157; Marshall, L. (1997) *J. Biol. Chem.* 272(2): 759-765; Anderson, K. M. et al. (1997) *J. Biol. Chem.* 272(48): 30504-30511; Li, Q. and Cathcart, M. K. (1997) *J. Biol. Chem.* 272(4): 2404-2411; Zhao, X. et al. (2002) *J. Biol. Chem.* 277(28): 25385-25392].

The present inventor designed and described new anti-$cPLA_2\alpha$ antisense oligonucleotides, which were more efficient in the inhibition of $cPLA_2\alpha$ expression, as well as in the inhibition of pro-inflammatory processes, than the ones previously reported [WO2005/101968]. In the present study, the inventor demonstrates that these antisense oligonucleotides are effective in the inhibition of proliferation of human cancer cell lines.

Thus, it is an object of the present invention to provide the use of anti-$cPLA_2\alpha$ antisense oligonucleotides as an anti-neoplastic agent.

Other uses and objects of the invention will become clear as the description proceeds.

SUMMARY OF THE INVENTION

Thus, in a first aspect, the present invention relates to the use of an inhibitor of $cPLA_2\alpha$ expression in the preparation of a pharmaceutical composition for the treatment of cancer, as well as for the treatment of a malignant proliferative disease In a second aspect, the present invention relates to the use of an inhibitor of cPLA$_2$α expression in the preparation of a pharmaceutical composition for the inhibition of cancer cell proliferation.

In one embodiment, said inhibitor of cPLA$_2$α expression is any one of a cPLA$_2$α specific ribozyme, an RNA sequence used for RNA interference of the cPLA$_2$α gene, and an antisense oligonucleotide directed against cPLA$_2$α. Preferably, said inhibitor of cPLA$_2$α expression is an antisense oligonucleotide directed against cPLA$_2$α, denoted by any one of SEQ. ID. No. 1, SEQ. ID. No. 3, SEQ. ID. No. 6, SEQ. ID. No. 2, SEQ. ID. No. 4 and SEQ. ID. No. 5.

In another embodiment, said malignant proliferative disease is selected from the group consisting of colon cancer, liver cancer, prostate cancer, lung cancer and brain cancer. In particular, said cancer cell is selected from the group consisting of colon, liver, prostate, lung cells and neuron cells.

The invention will be further described on the hand of the following figures, which are illustrative only and do not limit the scope of the invention which is defined by the appended claims.

BRIEF DESCRIPTION OF THE FIGURES

FIG. 1:
The effect of a combination of antisenses 4+2+10 (final concentration 1 μM) on the proliferation of human epithelial cancer cell lines is shown. The results are expressed as % of control, and are from one representative experiment out of three.

FIG. 2:
The effect of a combination of antisenses 4+2+10 (final concentration 1 μM) on the proliferation of a human endothelial cancer cell line and normal endothelial cells, as well as on cPLA$_2$α expression is shown. The house keeping protein β actin was blotted to show equal amount of protein in each lane. The results are expressed as % of control, are from one representative experiment out of three.

FIG. 3:
The effect of a combination of antisense 4+2+10 (final concentration 1 μM) on proliferation of human macrophage cancer cell line U937, normal human peripheral blood monocytes, human peritoneal macrophages and the leukemic PLB-985 cell line is shown. The effect of the antisense treatment on cPLA$_2$ expression in U937 and monocytes is shown in comparison to the cytosolic oxidase component p47$^{phox}$ to demonstrate equal amount of protein in each lane. Results are expressed as % of control, and are from one representative experiment out of three.

DETAILED DESCRIPTION OF THE INVENTION

The following abbreviations are used herein:
AA Arachidonic acid
cPLA$_2$ Cytosolic Phospholipase A$_2$
HUVEC Human Umbilical Vein Endothelial Cells In WO2005/101968, the present inventor designed and described new anti-cPLA$_2$α antisense oligonucleotides, which were capable of inhibiting pro-inflammatory processes. In the present study, as shown in Example 1 and FIGS. 1-3, the present inventor demonstrates that these antisense oligonucleotides are also effective in the inhibition of proliferation of human cancer cell lines.

The inventor's early findings showed that the rate of proliferation and the differentiation of cPLA$_2$α knock out PLB-985 cell line was normal [Dana, R. et al. (1998) *J. Biol. Chem.* 273:441-5;], indicating that cPLA$_2$α has no role in development of cancer, specifically leukemia. cPLA$_2$α is expressed in several tissue types, and its expression has been shown to be elevated under inflammatory conditions without any relationship to malignancy. In addition, homozygous deletion of cPLA$_2$α produced a significant reduction in tumor number in the murine small intestine, whereas no significant effect was observed in the large intestine.

In the present invention, the results show that the antisense oligonucleotides against cPLA$_2$α that are efficient against inflammation are also potent in arresting proliferation of several cancer cell types, indicating their potential use in the treatment of those cancers, in addition to their effect against inflammation. Interestingly, the results show that the involvement of cPLA$_2$α with cancer is tissue specific and there are differences in the sensitivity of cancer cells from different origins. For example, the anti-cPLA$_2$α antisense oligonucleotides inhibited proliferation of epithelial cancer cells from colon, liver and lung origin, but not of epithelial breast cancer cells.

It is understood from the results presented herein, that cPLA$_2$α is a potential target for cancer treatment, since its inhibition results in less proliferation of cancer cells. Thus, any inhibitor of cPLA$_2$α is a potential drug for cancer treatment.

Hence, the present invention provides the use of inhibitors of cPLA$_2$α, either per se or in the form of a composition, for the treatment of cancer and/or malignant proliferative disorders.

As herein defined, said inhibitor of cPLA$_2$α expression is any agent which is capable of blocking or hindering the expression of the cPLA$_2$α gene, particularly by interacting with its mRNA. Thus, said inhibitor may be a cPLA$_2$α-specific ribozyme, a double-stranded nucleotide sequence used for RNA interference of the cPLA$_2$α gene, or an antisense oligonucleotide directed against cPLA$_2$α. Antisense nucleotides are preferably nuclease resistant.

As understood herein, an antisense oligonucleotide is a nucleotide comprising essentially a reverse complementary sequence to a sequence of cPLA$_2$α mRNA. The nucleotide is preferably an oligodeoxynucleotide, but also ribonucleotides or nucleotide analogues, or mixtures thereof, are contemplated by the invention. The antisense oligonucleotide may be modified in order to enhance the nuclease resistance thereof, to improve its membrane crossing capability, or both. The antisense oligonucleotide may be linear, or may comprise a secondary structure. It may also comprise enzymatic activity, such as ribozyme activity.

Preferably, said inhibitor of cPLA$_2$α expression is an antisense oligonucleotide directed against the 5' region of the open reading frame of the cPLA$_2$α mRNA sequence, having the sequence as denoted by any one of SEQ. ID. No. 1, SEQ. ID. No. 2, SEQ. ID. No. 3, SEQ. ID. No. 4, SEQ. ID. No. 5 and SEQ. ID. No. 6, as detailed in Table 1.

Each antisense oligonucleotide may be utilized alone, or in combination with one or more of the herein described anti-cPLA$_2$α antisense oligonucleotides.

Thus, the present invention provides the use of cPLA$_2$α expression inhibitors in the preparation of a pharmaceutical composition for the inhibition of cancer cell proliferation and for the treatment of cancer and/or proliferative malignant disorders.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Pharmaceutical compositions comprising as an active agent cPLA$_2$α expression inhibitors may generally further comprise a diluent, and/or a buffering agent, i.e. an agent which adjusts the osmolarity thereof, and optionally, one or more carriers, stabilizers, excipients and/or additives as known in the art, e.g., for the purposes of adding flavors, colors, lubrication, or the like to the pharmaceutical composition.

Carriers may include starch and derivatives thereof, cellulose and derivatives thereof, e.g., microcrystalline cellulose, xantham gum, and the like. Lubricants may include hydrogenated castor oil and the like.

A preferred buffering agent is Tris, consisting of 10 mM Tris, pH 7.5-8.0, which solution is also adjusted for osmolarity.

The preferred cPLA$_2$α expression inhibitors to be used in the preparation of a pharmaceutical composition for the treatment of cancer or proliferative malignant disorder are the anti-cPLA2 antisense oligonucleotides described herein.

For in vivo use, the antisense oligonucleotides are suspended is sterile distilled water or in sterile saline.

Preferred modes of administration of the pharmaceutical composition of the invention are by subcutaneous, intraperitoneal, intravenous or intramuscular injection.

It is to be therefore understood that the compositions of the invention are useful for treating or inhibiting tumors at all stages, namely tumor formation, primary tumors, tumor progression or tumor metastasis.

As used herein to describe the present invention, "malignant proliferative disorder", "cancer", "tumor" and "malignancy" all relate equivalently to a hyperplasia of a tissue or organ. Malignancies of other tissues or organs may produce solid tumors. In general, the composition prepared with the herein described antisense oligonucleotides are to be used in the treatment of solid tumors, for example, carcinoma, melanoma, sarcoma, and lymphoma.

The inventor's results suggest that the antisense oligonucleotides against cPLA$_2$α are an efficient strategy for treatment of different cancer diseases, including colon cancer, lung cancer, liver cancer and prostate cancer, as well as brain cancer (data not shown).

Finally, the present invention provides a method of treatment of cancer or proliferative malignant or non-malignant disorders, said method comprising administering a therapeutically effective amount of a cPLA$_2$α expression inhibitor or a composition comprising the same, to a subject in need.

The term "effective amount" means an amount necessary to achieve a selected result, which at present, involves the amount of a cPLA$_2$α expression inhibitor necessary for treating cancer or proliferative malignant or non-malignant disorders.

Said therapeutic effective amount, or dosing, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC$_{50}$, found to be effective in in vitro as well as in in vivo animal models. In general, dosage is from 0.01 µg to 10 mg per kg of body weight, and may be given once or more daily, weekly, monthly or yearly, or even once every 2 to 20 years. Persons of ordinary skill in the art can easily estimate repetition rates for dosing based on measured residence times and concentrations of the antisense oligonucleotide in bodily fluids or tissues.

The terms "treat, treating or treatment" as used herein mean ameliorating one or more clinical indicia of disease activity in a patient having cancer or a proliferative malignant or non-malignant disease. "Treatment" refers to therapeutic treatment.

By "patient" or "subject in need" is meant any mammal for which cancer treatment is desired in order to overcome said malignant or non-malignant disease.

Usually, a "therapeutically effective amount" is also determined by the severity of the disease in conjunction with the preventive or therapeutic objectives, the route of administration and the patient's general condition (age, sex, weight and other considerations known to the attending physician).

Various methods of administration may be used for delivering the antisense oligonucleotide of the invention to a subject in need. Oligonucleotides may be delivered via intravenous (i.v.), intramuscular (i.m.) intraperitoneal (i.p.) injections, orally (in liquid form or prepared as dosage unit forms like capsules, pills, lozenges, etc.). In order to be effective therapeutically, oligonucleotides should be prepared in a way that would enable their stability in the system following injection, or yet more preferably, following oral administration.

The above described method is intended to be used to treat subjects suffering from hematological malignancies, cancer and metastatic solid tumors.

As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, congenital malformations, disabilities, syndromes, symptoms, deviant behaviors, and atypical variations of structure and function, chronic or permanent health defects resulting from disease.

The terms "disease", "disorder", "condition" and "illness" are equally used herein.

Therefore, according to a preferred embodiment, the inhibitor of cPLA$_2$ expression, which is preferably an anti-cPLA$_2$ antisense oligonucleotide, or a composition comprising the same, may be used for the treatment or inhibition of solid tumors such as colon cancer, lung cancer, liver cancer, prostate cancer and brain cancer, as well as cancer of the lip and oral cavity, pharynx, larynx, paranasal sinuses, major salivary glands, thyroid gland, esophagus, stomach, small intestine, colorectum, anal canal, gallbladder, extrahepatic bile ducts, ampulla of vater, exocrine pancreas, pleural mesothelioma, bone, soft tissue sarcoma, carcinoma and malignant melanoma of the skin, vulva, vagina, cervix uteri, corpus uteri, ovary, fallopian tube, gestational trophoblastic tumors, penis, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, spinal cord, vascular system, hemangiosarcoma and Kaposi's sarcoma.

An "in vivo" treatment, as used herein, refers to a process that takes place within a living organism. An "ex vivo" treatment relates to a process taking place outside of a living organism or body, e.g. the treatment of cells, which treated cells may be returned to the same or to a different living organism.

As used in the specifications and the appended claims and in accordance with long-standing patent Law practice, the singular forms "a" "an" and "the" generally mean "at least one", "one or more", and other plural references unless the context clearly dictates otherwise. Thus, for example "a cell", "a peptide" and "an immune modulator agent" include mixture of cells, one or more peptides and a plurality of adjuvants of the type described.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

General Methods of Molecular Biology

A number of methods of the molecular biology art are not detailed herein, as they are well known to the person of skill in the art. Such methods include PCR, expression of cDNAs, transfection of mammalian cells, and the like. Textbooks describing such methods are, e.g., Sambrook et al. (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological techniques are not in each instance described herein in detail, like for example Western Blot, as they are well known to the person of skill in the art. See, e.g., Harlow and Lane (1988) Antibodies: a laboratory manual, Cold Spring Harbor Laboratory.

cPLA$_2$α Antisense Oligonucleotides

TABLE 1

Oligonucleotides used in the following examples

| Oligo-nucleotide | Sequence 5'-3' | Sequence ID. No. |
|---|---|---|
| C2 | ttcaaaggtctcattccaca | SEQ. ID. No. 1 |
| C3 | cactataatgtgctggtaag | SEQ. ID. No. 2 |
| C4 | caaaacattttcctgattagg | SEQ. ID. No. 3 |
| C8 | cacagggtttatgtcattat | SEQ. ID. No. 4 |
| C9 | ccgtaaacttgtgggaatac | SEQ. ID. No. 5 |
| C10 | gctgtcaggggttgtag | SEQ. ID. No. 6 |
| Control - sense | caccaaagtgacaaaggg | SEQ. ID. No. 7 |
| Control - 1 | gctttaacattttattttatttg | SEQ. ID. No. 8 |
| Control - 2 | acagttcttggcatttgttctc | SEQ. ID. No. 9 |
| Control - 3 | gtagaagaggtactttaagyttg | SEQ. ID. No. 10 |
| Control - 4 | agtcaatggcatcgcggggctgg | SEQ. ID. No. 11 |

Note:
the underline shows phosphorothioated nucleotides.

Prior to use, the oligonucleotides were purified by HPLC and tested for purity by mass spectrometry (Sigma, UK). The oligonucleotides carried phosphorothioate modifications on the last 3 bases at both 5' and 3' ends (as indicated by underline, Table 1), and were engineered using computer based approach using RNADraw V1.1 [Mazura Multimedia, Sweden] for the first 400 hundred base pairs (N-terminal) of cPLA$_2$α mRNA (Table 1). As marked by the underline, oligonucleotides C8 and C9 have a modification also in the middle of the sequence.

Cell Culture

Five different human cancer cell lines from different epithelial origins were studied: HT-29—colorectal adenocarcinoma; MCF-7—breast adenocarcinoma; HepG2—hepatocellular carcinoma; PC-3—prostate adenocarcinoma; A549 cells—lung adenocarcinoma. In addition, human umbilical endothelial cell-derived transformed cell line (ECV 304 cells) was analyzed in comparison to normal human umbilical vein endothelial cells (HUVECs). U937 macrophages derived from histiocytic lymphoma were studied in comparison with cultured peripheral blood monocytes, human peritoneal macrophages and PLB-985 cells promyeloblast-derived from acute promyelocytic leukemia. Cells were cultured in RPMI 1640 media containing 10% fetal bovine serum and 1% antibiotic solution at 37° C. in a humidified atmosphere containing 5% CO2.

All cells were obtained from the American Type Culture Collection (Rockville, Md.).

Proliferation Assay

Cells were plated at a density of $10^4$ cells/well on a 96-well plate. At 24 h after seeding, antisense oligonucleotides were added at a final concentration of 1 μM to the culture medium.

Cell viability was assayed colorimetrically on days 1, 3, and 5 of drug treatment using an MTT-based test [Vistica, D. et al. (1991) *Cancer Research* 51:2515-20]. In brief, MTT was added to each well at a concentration of 500 μg/ml and plates were incubated for 4 h at 37° C. After 4 h, media were aspirated and cells were lysed with 400 μl of DMSO. Cells were incubated for a further 10 min at 37° C. with gentle shaking. Absorbance readings at 570 nM were determined using a computer-controlled microplate analyzer. In addition, cell number was determined by trypan blue exclusion.

cPLA$_2$α Expression

Cell lysates were prepared (using 1% Triton X-100, 50 mM HEPES (pH 7.5), 150 mM NaCl, 1 mM EDTA, 1 mM EGTA, 10% glycerol, 25 mM NaF, 10 μM ZnCl$_2$, 1 mM PMSF, and 100 μM leupeptin). 100 μg of protein from cell lysates were separated by electrophoresis on 7.5% polyacrylamide SDS gels and blotted onto nitrocellulose. The detection of cPLA$_2$α protein was performed using rabbit antibodies raised against a GST-cPLA$_2$α fusion protein.

Example 1

Figure 1A:
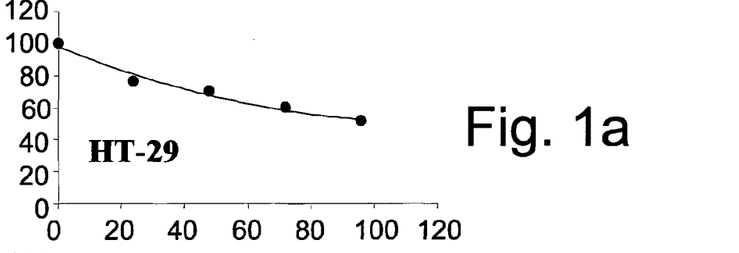
Figure 1B:
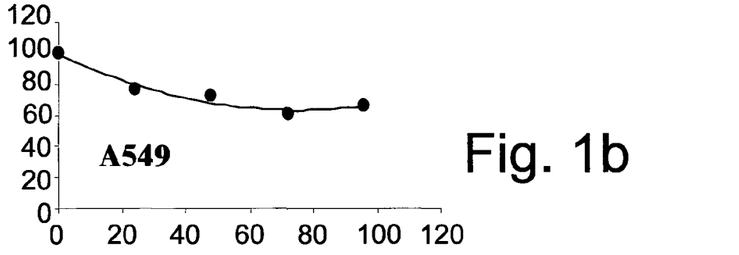
Figure 1C:
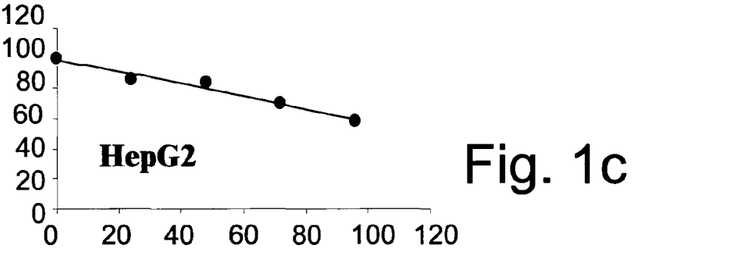
Figure 1D:
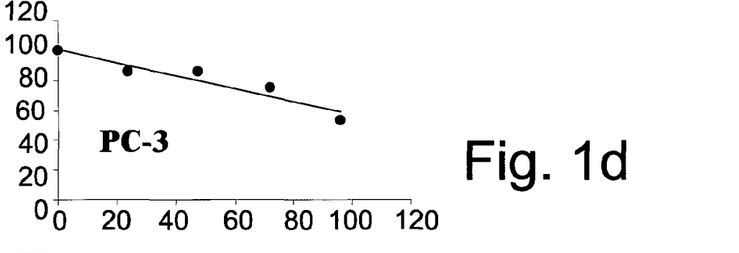
Figure 1E:
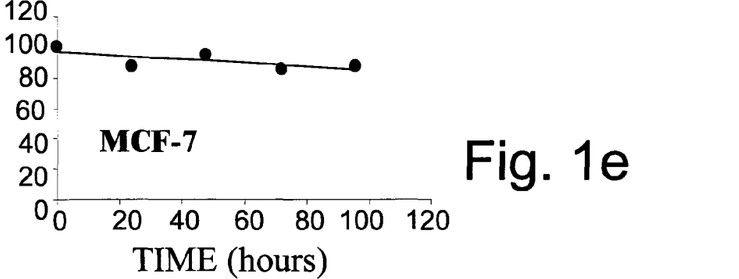
Figure 2A:
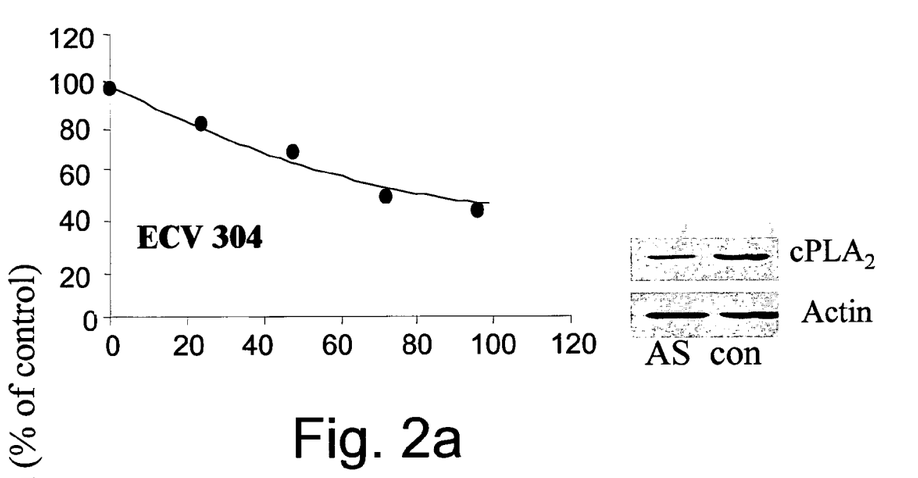
Figure 2B:
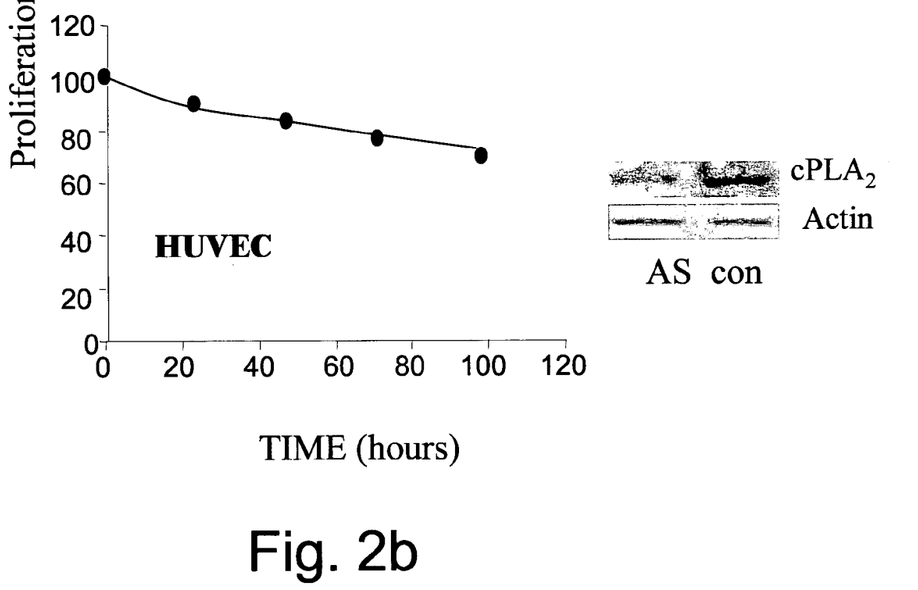
Figure 3A:
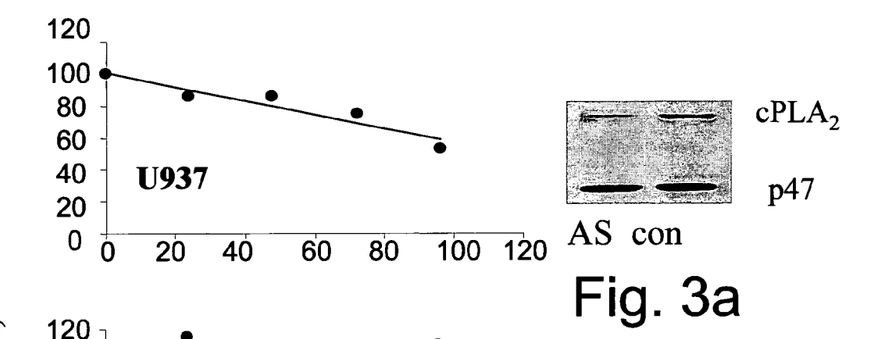
Figure 3B:
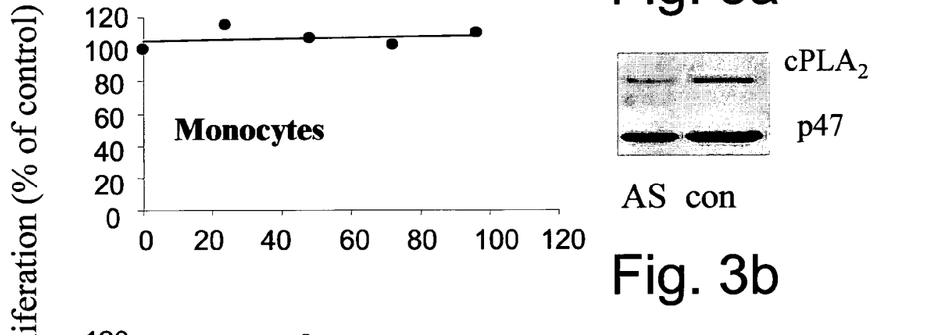
Figure 3C:
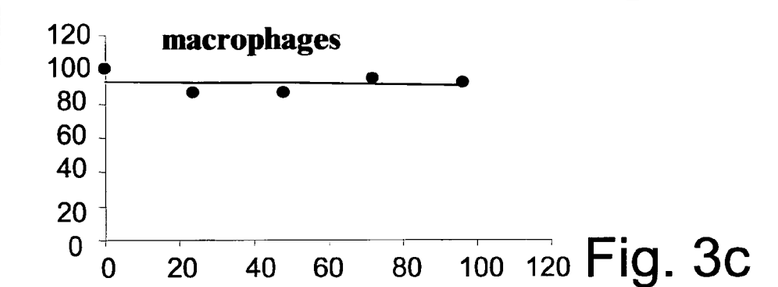
Figure 3D:
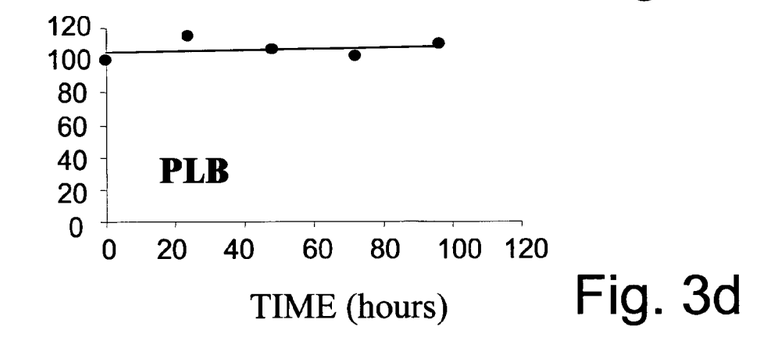

The effect of the partially phosphorothioated antisense oligonucleotides against cPLA$_2$α (cPLA$_2$α antisense) on cell proliferation was studied in different cell types. The results present the effect of a combination of cPLA$_2$α antisense oligonucleotides, including C2, C4 and C10 (see Table 1) which were shown to be effective in inhibiting cPLA$_2$α at a final concentration of 1 µM. The effect of antisense treatment on proliferation during 4 days was tested when added once at time zero (FIG. 1). The results are expressed as % of control, which was treated with scrambled antisenses. Daily addition of antisense during the 4 days of the study did not significantly change the results (not shown). As shown in FIG. 1, the antisense against cPLA$_2$α caused a significant inhibition of cell proliferation of the colon (HT-29), liver (Ilep G2), prostate (PC-3) and lung cancer cells (A549), but not of breast cancer cells (MCF-7). FIG. 2 shows that the antisense treatment inhibited the proliferation of transformed cell line-ECV 304 more effectively than of the normal cells (HUVEC), although the antisense in reduced cPLA$_2$α activity in both cell types. The antisense inhibited the proliferation of U937 cells (monocytes-macrophages from histiocytic lymphoma) but not peripheral blood monocytes or peritoneal macrophages, although in both cell types cPLA$_2$α expression was inhibited. In addition, the antisense did not inhibit the proliferation of PLB-985 cells (promyelocytic leukemia) as shown previously in a cPLA$_2$α knock out PLS-985 cell line [Dana, R. et al. (1998) *J. Biol. Chem.* 273:441-5]

The results presented herein strongly indicate that antisense oligonucleotides against cPLA$_2$α are an efficient strategy for treatment of different cancer diseases, including colon cancer, lung cancer, liver cancer and prostate cancer.

Example 2

Induction of Colon Cancer

Five-week-old male A/J mice are housed in a temperature-controlled environment (23° C.). with a 12 h light/dark cycle. After an acclimation period of 1 week, mice are divided randomly into two groups. One group is treated via i.p. injection with Azoxymethane (AOM, Sigma, St Louis, Mo.) dissolved in saline, at a dose of 10 mg/kg of body weight once per week during 6 weeks. The other group is treated with saline and served as vehicle controls. Mice are killed every week between 20-24 weeks after the last dose. cPLA$_2$α antisense treatment is administered both to the AOM-treated and to the control mice via i.v., 2 mg/ml everyday from week 19 until after the last dose. The entire colon is removed and flushed with ice-cold PBS buffer. Colons are slit open longitudinally. Colon tumors from the AOM treatment group and normal distal colons from the control group are dissected and tissues are divided into macroscopically similar portions. The portions for RNA and protein analysis are immediately frozen in liquid nitrogen and stored at −80° C. The remaining portion, for paraffin embedding, is fixed in 10% neutral-buffered formalin for 6 h and embedded in paraffin for subsequent histopathological examination and immunostaining.

Example 3

Induction of Lung Carcinogenesis

Mice are injected i.p. once per week for 6 weeks with 1 mg urethane (Sigma, St Louis, Mo.) dissolved in 0.9% NaCl/g of body weight, weighed weekly, and observed daily for the duration of the study to assess their health. Nineteen weeks after the initial carcinogen injection, tumors are enumerated and examined under a dissecting microscope, and tumor diameters measured with digital calipers. Mice are also subjected to this carcinogenesis regimen to obtain tissue samples for immunohistochemistry and immunoblotting.

While this invention has been described in terms of some specific examples, many modifications and variations are possible. It is therefore understood that within the scope of the appended claims, the invention may be realized otherwise than as specifically described.

The invention claimed is:

1. A method for treating colon cancer in a mammalian human subject in need thereof which comprises administering to the subject a pharmaceutical composition having an active agent which consists of an inhibitor of cPLA$_2\alpha$ expression wherein said inhibitor is selected from the group consisting of a cPLA$_2\alpha$-specific ribozyme, a double stranded nucleotide sequence used for RNA interference of the cPLA$_2\alpha$ gene, and an antisense oligonucleotide directed against cPLA$_2\alpha$.

2. The method of claim 1, wherein said inhibitor of cPLA$_2\alpha$ expression is an antisense oligonucleotide directed against cPLA$_2\alpha$.

3. The method of claim 2, wherein said antisense oligonucleotide is denoted by any one of SEQ. ID. No. 1, SEQ. ID. No. 3, SEQ. ID. No. 6, SEQ. ID. No. 2, SEQ. ID. No. 4 or SEQ. ID. No. 5.

* * * * *